(12) United States Patent
Dzhavakhia et al.

(10) Patent No.: US 7,592,509 B2
(45) Date of Patent: Sep. 22, 2009

(54) ISOLATED DNA SEQUENCES AND POLYPEPTIDES INDUCING MULTIPLE RESISTANCE OF PLANTS TO PHYTOPATHOGENS AND PESTS

(76) Inventors: Vitaly Dzhavakhia, Mozhaiskoe Shosse 6-41, Bolshie Vyazemi, Moscow (RU) 143050; Alexei Filippov, Pos. Shkolny 5061, Bolshie Vyazemi, Moscow (RU) 143050; Konstantin Skryabin, Dmitry Ulyanov's Street 3-124, Moscow (RU) 119333; Tatiana Voinova, Pos. Shkolny 4-74, Bolshie Vyazemi, Moscow (RU) 143050; Daria Shumilina, Mozhaiskoe shosse 4-3, Bolshie Vyazemi, Moscow (RU) 143050; Ksenia Kromina, Kasimovskaya Street 41-13, Moscow (RU) 115404; Maria Kouznetsova, Mozhaiskoe shosse 4-3, Bolshie Vyazemi, Moscow (RU) 143050; Olga Shulga, Molodevnaya 31-48, Khimki, Moscow (RU) 141400; Mikhail Pridanniko, Institute Street 16-258, Bolshie Vyazemi, Moscow (RU) 143050; Natalia Battchikova, Tikankatu 12, Turku (FI) 20610; Timo Korpela, Kraatarinkatu 1D 42, Turku (FI) 20610

( * ) Notice: Subject to any disclaimer, the term of this patent is extended or adjusted under 35 U.S.C. 154(b) by 189 days.

(21) Appl. No.: 10/583,066

(22) PCT Filed: Dec. 17, 2004

(86) PCT No.: PCT/FI2004/000766

§ 371 (c)(1),
(2), (4) Date: Oct. 6, 2006

(87) PCT Pub. No.: WO2005/061533

PCT Pub. Date: Jul. 7, 2005

(65) Prior Publication Data

US 2007/0192898 A1    Aug. 16, 2007

(30) Foreign Application Priority Data

Dec. 22, 2003    (FI) ................... 20031880

(51) Int. Cl.
*C12N 15/31* (2006.01)
*C12N 15/82* (2006.01)
*A01H 5/00* (2006.01)
*C07K 14/21* (2006.01)
*A01N 63/00* (2006.01)
*C12N 1/21* (2006.01)
*C12N 5/04* (2006.01)
*C07K 14/195* (2006.01)
*C07K 14/325* (2006.01)

(52) U.S. Cl. ............ 800/301; 800/279; 800/278; 800/298; 800/288; 536/23.6; 435/320.1; 435/468; 435/419; 435/69.1; 435/252.3; 530/350; 514/12

(58) Field of Classification Search .......... None
See application file for complete search history.

(56) References Cited

FOREIGN PATENT DOCUMENTS

WO    WO97/05165    *  2/1997

* cited by examiner

*Primary Examiner*—Medina A Ibrahim
(74) *Attorney, Agent, or Firm*—Dodds & Associates; John H. Dodds; L. Susanne Somesalo

(57) ABSTRACT

The invention relates to isolated DNA sequences encoding MF3 polypeptides that induce multiple resistance in plants toward a variety of viral and microbial infections and against pests and a method of obtaining transgenic plants expressing MF3 polypeptides. The invention also relates to a method of isolating and purifying an MF3 polypeptide from bacterial cells expressing the polypeptide and its use as a plant protectant with or without carrier agent.

15 Claims, 1 Drawing Sheet

SEQUENCE LISTING

```
<160> NUMBER OF SEQ ID NOS: 6

<210> SEQ ID NO 1
<211> LENGTH: 161
<212> TYPE: PRT
<213> ORGANISM: Pseudomonas fluorescence strain 197

<400> SEQUENCE: 1

Met Leu Ile Ala Ala Asn Lys Ala Val Ser Ile Asp Tyr Thr Leu Thr
1               5                   10                  15

Asn Asp Ala Gly Glu Val Ile Asp Ser Ser Ala Gly Gly Ala Pro Leu
            20                  25                  30

Val Tyr Leu Gln Gly Ala Gly Asn Ile Ile Pro Gly Leu Glu Lys Ala
        35                  40                  45

Leu Glu Gly Lys Ala Val Gly Asp Asp Leu Glu Val Ala Val Glu Pro
    50                  55                  60

Glu Asp Ala Tyr Gly Glu Tyr Ala Ala Glu Leu Val Ser Thr Leu Ser
65                  70                  75                  80

Arg Ser Met Phe Glu Gly Val Asp Glu Leu Glu Val Gly Met Gln Phe
                85                  90                  95

His Ala Ser Ala Pro Asp Gly Gln Met Gln Ile Val Thr Ile Ala Asp
            100                 105                 110

Leu Asp Gly Asp Val Thr Val Asp Gly Asn His Pro Leu Ala Gly
        115                 120                 125

Gln Arg Leu Asn Phe Lys Val Lys Ile Val Asp Ile Arg Asp Ala Ser
    130                 135                 140

Gln Glu Glu Ile Ala His Gly His Val His Gly Glu Gly Gly His His
145                 150                 155                 160
```

His

<210> SEQ ID NO 2
<211> LENGTH: 486
<212> TYPE: DNA
<213> ORGANISM: pseudomonas fluorescence strain 197

<400> SEQUENCE: 2

```
atgctgatcg ccgccaataa ggctgtctcc atcgactata ccctgaccaa cgacgctggt      60
gaggtcatcg acagctccgc cggcggcgct ccgctggttt acctgcaagg tgcaggcaac     120
atcatcccgg gcctggaaaa agccctggaa ggcaaagctg tcggcgacga cttggaagtg     180
gccgttgagc cggaagatgc ttacggcgaa tacgccgccg agctggtcag caccctgagc     240
cgcagcatgt tcgaaggcgt tgacgagctg aagtcggca  tgcagttcca tgcttcggcg     300
ccggacggcc agatgcagat cgtcaccatt gctgacctgg acggcgacga cgtcaccgtt     360
gatggcaacc accctctggc cggtcagcgc ctgaacttca aggttaagat cgttgatatc     420
cgtgacgcca gccaggaaga aatcgctcat ggccacgtcc atggcgaagg tggccatcac     480
cactga                                                                486
```

<210> SEQ ID NO 3
<211> LENGTH: 57
<212> TYPE: PRT
<213> ORGANISM: pseudomonas flurescence strain 197

<400> SEQUENCE: 3

```
Gly Ala Pro Leu Val Tyr Leu Gln Gly Ala Gly Asn Ile Ile Pro Gly
1               5                   10                  15

Leu Glu Lys Ala Leu Glu Gly Lys Ala Val Gly Asp Asp Leu Glu Val
            20                  25                  30

Ala Val Glu Pro Glu Asp Ala Tyr Gly Glu Tyr Ala Ala Glu Leu Val
        35                  40                  45

Ser Thr Leu Ser Arg Ser Met Phe Glu
    50                  55
```

<210> SEQ ID NO 4
<211> LENGTH: 45
<212> TYPE: PRT
<213> ORGANISM: pseudomonas fluorescence stain 197

<400> SEQUENCE: 4

```
Met Gln Ile Val Thr Ile Ala Asp Leu Asp Gly Asp Asp Val Thr Val
1               5                   10                  15

Asp Gly Asn His Pro Leu Ala Gly Gln Arg Leu Asn Phe Lys Val Lys
            20                  25                  30

Ile Val Asp Ile Arg Asp Ala Ser Gln Glu Glu Ile Ala
        35                  40                  45
```

<210> SEQ ID NO 5
<211> LENGTH: 25
<212> TYPE: DNA
<213> ORGANISM: artificial sequence
<220> FEATURE:
<223> OTHER INFORMATION: primer

<400> SEQUENCE: 5

```
ggaattccat atgctgatcg ccgcc                                            25
```

<210> SEQ ID NO 6

```
<211> LENGTH: 25
<212> TYPE: DNA
<213> ORGANISM: artificial sequence
<220> FEATURE:
<223> OTHER INFORMATION: primer

<400> SEQUENCE: 6
cccaagctta gtggtgatgg ccacc                                              25
```

ISOLATED DNA SEQUENCES AND POLYPEPTIDES INDUCING MULTIPLE RESISTANCE OF PLANTS TO PHYTOPATHOGENS AND PESTS

PRIORITY

This is national stage application under 35 U.S.C. section 371 of international application PCT/FI2004/000766 filed on Dec. 17, 2004 and published as WO2005/061533 on Jul. 7, 2005, said international application claiming priority of the Finnish national patent application FI20031880 filed on Dec. 22, 2003.

SEQUENCE LISTING

This application contains sequence data provided on a computer readable diskette and as a paper version. The paper version of the sequence data is identical to the data provided on the diskette.

FIELD OF INVENTION

The present invention relates to agriculture and horticulture, more specifically to protection of plants against viruses, bacteria, fungi, and other parasites. In particular, the invention describes bacterial proteins inducing general resistance of plants against microbial pathogens and animal parasites.

BACKGROUND OF INVENTION

Pathogenic microbes and pests are responsible for substantial economic losses in crop production worldwide. Current control practices against them each have severe drawbacks. In principle, breeding new varieties of crops, which are inherently more resistant to the pathogens, can prevent crop losses. In practice, however, each new variety is ultimately doomed to fail since pathogens slowly evolve a resistance. Application of synthetic non-natural chemicals pose a significant risk for ecology. Only very recently related molecules existing in nature have been introduced. However, such natural chemicals are expensive, demand special spraying tools and are labor-intensive.

During the last 2 decades, new approaches involving transgenic plants with certain alien genes have been developed to generate resistance to viral pathogens. Such plants involve, as a rule, expression of certain viral genes (for example, coat protein). Unfortunately, the acquired resistance is only effective against the specific viral strain that the plant is "vaccinated" against. For example, resistance to potato virus Y (PVY) was ineffective against other viral strains which differed by as little as 22% at the nucleotide level. Hence, this kind of resistance has limited practical applications because different pathogens dominate when the climate conditions and other factors change. Farmers expect that their investment in the costly seed materials should be profitable each year, not only during some years. Nevertheless, because of the lack of more universal solutions, such limited resistance has been engineered against different viruses in a wide range of crop species. Also the situation has to be seen from the increasingly important perspective of public opinion and fear regarding the use of transgenic plants: benefits must be positive enough to outweigh public concerns.

Systemic acquired resistance (SAR) is a resistance reaction first reported by Chester (1933). SAR is a common plant defense reaction in which a plant systemically produces various defense molecules such as lignin, phytoalexins and PR-proteins to prevent the spread of pathogens (reviewed by Sticher et al. 1997, Ann. Rev. Phytopathol. 35, 235-270). SAR can be induced within a few hours by many pathogenic microbes and the resistance then lasts for several weeks. SAR is a salicylic acid-dependent resistance reaction, but the primary role of salicylic acid in SAR is still unclear (Ryal et al. 1996, Plant Cell 8, pp. 1809-1819). Spread of the pathogen is confined to a small number of cells in plants with an established SAR; therefore the pathogens cannot, in practice, harm the plant.

Whereas there exists an enormous necessity for quick development of novel plant species with higher resistance against different diseases and parasites, and with a higher ecological safety, no such solution has been clearly offered. The present invention offers completely novel concepts for increasing the plant resistance based on our surprising finding that a certain protein from bacterial strains, the proteins termed as MF3, can trigger in plants a wide systemic resistance against including viruses, bacteria, fungi, insect pests, such as the Colorado potato beetle, and nematodes. The broad protective potential of MF3 is demonstrated by the experimental results justifying the claim that the protein can generate a full spectrum of plant resistance to pathogens and pests. While the effects of the discovered protein in plants resemble those of SAR, no mechanistic connection can be drawn for their relationship.

We discovered previously another protein with a distinctly different molecular structure than MF3; this previous protein originated from a *Bacillus thuringiensis* strain (MF2, Djavakhia V., et al. U.S. Pat. No. 6,528,480). Transgenic tobacco plants expressing MF2 possessed increased resistance to viruses and fungi (Tobacco Mosaic Virus and *Alternaria longipes*). In the present invention we found a totally different microbial protein with improved activity and significantly wider applications. Therefore the present invention provides a significant improvement over our previous invention by showing that a novel molecule can induce multiple resistance to plants involving microbes, as well as insects and nematodes that, in particular, are known as serious plant parasites. We also show that MF3 can be used as the resistance inducer in various transgenic plants without any loss of crop productivity.

DETAILED DESCRIPTION OF THE INVENTION

Figure 1:
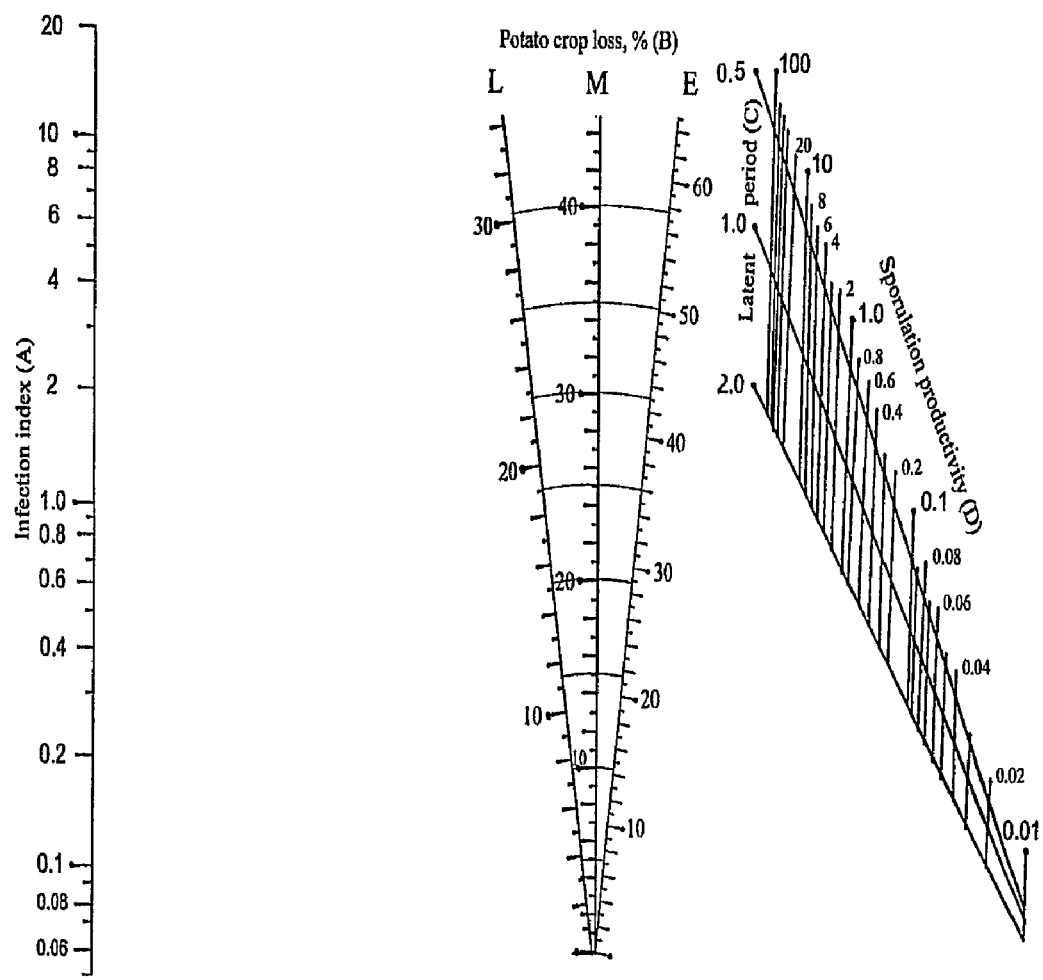
FIG. 1. Nomogram for determination of potato harvest losses from late blight disease as a result of premature dying off of leaves.

The key aspect of active defense of an organism against invading microbes or other pathogens is the ability to discriminate between self from non-self. In plants, the recognition-dependent disease resistance has been studied most thoroughly and most successfully in the cases that depend on the presence of specific resistance-genes, which confer resistance to particular races of plant pathogens. Several of these resistance genes were shown to be involved in the chemo-perception of factors specifically attributed with particular strains of pathogens. In addition, plants have a broader, more basal, surveillance involving sensitive perception systems for patterns characteristic for entire groups or classes of microorganisms, and they respond to these general elicitors with activation of signaling pathways for initiating defense mechanisms.

Possible examples of elicitors of protein nature are described in the present invention. There are known examples of proteins with resistance-inducing activities in the prior art. However, these proteins were isolated from infected plant tissues but specifically act only with a certain pair of host-pathogen interactions which is in contrast to the present invention In addition, contrary to the known proteins and resistance mechanisms, in the present invention we found bacterial protein molecules, termed MF3, with a known enzymatic activity, and said proteins do not participate in any definite known phytopathogenesis processes. Treatment of plant tissues with solutions of this protein led to an activation of resistance mechanisms.

An evident utility of MF3 is the construction of transgenic plants involving a weak expression of MF3. The most straightforward utility is, however, the production of MF3 in large quantities and its introduction within proper formulations and methods into plant cells.

The techniques of developing transgenic plants is well known from textbooks and the first transgenic plants were created already about three decades ago. Genetic engineering technique have helped investigators to gain critical insights into the fundamental processes that govern the development of plants and the first commercial introductions of such genetically modified plants are now in public use.

One of the most promising traits that gene transfer offers is resistance to diseases. Exciting results have been achieved in creating plants resistant to viruses, an important matter because currently no direct way to treat virus-infected plants exists. The experiments with genetically modified plants have shown that expression of the virus genes, as a rule, confers resistance only to the same virus strains (see review by Baulcombe, 1994). In each of these cases the problem of limited resistance causes concern in the practical application of these plants. The problem can be overcome by using genes of factors, which induce multiple resistance in plants, described in the present invention.

We isolated a protein MF2 from a *Bacillus thuringiensis* strain that induced resistance against viral and fungal infections of plants (Djavakhia V., et al. U.S. Pat. No. 6,528,480). In the present invention, we surprisingly found that it is not only *Bacillus thuringiensis* that may contain such an inducer. By applying specific novel screening methods to a very large number of soil microbes, we managed to isolate from a strain of *Pseudomonas* fluorescence a new inducer MF3. Strikingly, it was shown that it induces, at an extremely low concentration, general resistance of various plants to not only viral but also bacterial and fungal infections. Later it was shown that MF3 induces resistance to even nematodes and insect pests both by direct introduction of MF3 to plants through the leave cuticle and by an endogenous generation of MF3 in transgenic plants. The protein structures of MF2 and MF3 have no obvious sequence homologies. The only common feature is that they are both thermostable. Their molecular masses are also different: MF2 has molecular mass of 7239 Daltons; molecular mass of MF3 is around 17600 Daltons. MF3 is a novel protein sequence, but it appeared to resemble the most closely the enzyme peptidyl-prolyl cis-trans isomerase SlyD from *Pseudomonas aeruginosa.*

Peptidyl-prolyl cis-trans isomerases are in animals crucial in protein phosphorylation (see review by Zavyalov, V. et al. APMIS Vol. 103, pp. 401-415, 1995). Because there may exist common molecular links or correlations between resistance mechanisms in animal and plant kingdoms, it is possible that MF3 forms a key to the molecular mechanisms of plant resistance and has thus a general value as a molecular tool. Therefore, MF3 can be used in solving different phytopathological problems.

Preparations of MF3 can be effectively exploited in meristem culture technology for obtaining microbe-free plantlets by spraying a proper formulation of MF3 to meristem cultures, or by using MF3, or active peptides derived from it, possibly in a combination with heat treatment of the cell cultures. The use of this ecologically pure, non-phytotoxic substance could be effective for obtaining microbe-free clones of various agricultural plants. Knowledge of the structure of MF3 provides the possibility for making gene constructs for obtaining transgenic plants resistant to viral and other diseases.

There are clear advantages of transgenic plants containing MF3 expression. It is known that transgenic plants that contain parts of a viral genome have, as a rule, specific resistance to the particular virus in concern. The micro-organism used according to the present invention does not have any apparent structural relation. We have shown here that MF3 induces non-specific resistance of tobacco plants against Tobacco Mosaic Virus (TMV), Potato Virus X (PVX), and Potato Virus Y (PVY). Moreover, treatment of potato plants with MF3 led to induction of resistance against the late blight disease caused by *Phytophthora infestans*. It was also shown that the treatment of potato tubers with MF3 led to the induction of resistance against bacterial soft rot disease (*Erwinia carotovora*). In addition, MF3 induced resistance of rice plants against the rice blast disease caused by *Pyricularia oryzae*. Moreover, MF3 induced resistance of wheat plants against *Fusarium culmorum* and *Septoria nodorum*. As shown by the specific examples, also resistance against nematodes and insects were induced. It is highly probable that the resistance includes insects and in their different developmental forms, such as eggs, larvae and adults. Such different developmental stages attack plants at different locations (e.g. roots, foliae). Likewise, as shown by specific examples, a wide spectrum of different plants form resistance by the in vitro or in vivo introduction of MF3 into their cells or intercellular spaces. It is to be noted that MF3 can also have specific receptors inside of the plant tissue. Therefore, the present invention should be considered as the expression of universal protection of plants against different plant parasites and plant diseases.

The DNA sequence coding MF3 protein can be cloned into any cloning and/or expression vector for any organism, form bacteria to higher eukaryotes, including plants, with the help of commonly used genetic engineering methods, as described fo, for example in J. Sambrook, E. F., Frisch and T. Maniatis, Molecular Cloning: A Laboratory Manual $2^{nd}$ ed. (Cold Spring Harbor, N.Y.: Cold Spring Harbor Laboratory Press, 1989) We cloned the gene encoding MF3 and determined the gene sequence (SEQ ID NO: 2). We also determined the amino acid sequence of MF3 protein (SEQ ID NO: 1). *Escherichia coli* strain over-expressing MF3 was designed based on these results.

A further objective of the present invention is a method for isolation and purifying proteins possessing antiviral, antibacterial, antifungal, general antimicrobial, anti-nematode, and anti-insect activities from preferably a genetically modified microbe expressing said protein(s). Such method comprises:

(a) cultivating the microbial producer strain and extracting then the cells with an appropriate buffer solution at an elevated temperature, preferably on a boiling water bath, in order to eliminate the main part of the temperature sensitive substances from the extraction medium;

(b) precipitating crude MF3 polypeptide at low temperature with an appropriate precipitant to eliminate lower molecular weight organic substances from the protein fraction;

(c) fractionating re-dissolved precipitate by an anion exchange chromatography column, and collecting fractions with antimicrobial, anti-nematode and/or anti-insect activities;

(d) performing PAGE electrophoresis of the protein fractions with antiviral, or antibacterial, or anti-fungal, anti-nematode and/or anti-insect activities;

(e) recovering the protein eluted from the gel.

Whereas the above-described preferable method of antimicrobial protein purification can be modified, the essential features of the method shall include heat treatment at temperatures between 60-110° C. Also methods of measuring said biological activities in different fractions are equally essential. Different applications of anti-microbial proteins do not demand as pure protein as is described in the preferable purification method. In the heating step, the microbial cells, such as *Pseudomonas fluorescence*, are preferably extracted with a potassium-phosphate buffer, pH 7.4, containing EDTA, PMSF (phenyl methyl sulphonyl fluoride), ME (beta-mercaptoethanol) and Triton X-100 (polyoxyethylene ether). The precipitation is preferably carried out at temperatures between 2° C. and 6° C. with ice-cold chloroform and/or propanol and/or ammonium sulphate solution.

A further object of the invention is the use of MF3 as a plant protectant against various microbes. MF3 is preferably used with formulating substances including stabilizers, carriers, and/or adjuvants. Because MF3 is relatively stable, such additives are mainly aimed at helping the active ingredients to carry the active protein or its active fragments into plant cells and/or make them available to receptors. The formulation techniques for various plant protectants are known from prior art, as described by N. M. Golishin, 1982.

We have shown plant protectant activity of MF3 on tobacco plants against Tobacco Mosaic Virus (TMV), Potato Virus X (PVX), and Potato Virus Y (PVY). We have also shown protectant activity on potato plants against *Phytophthora infestans* and *Erwinia carotovora*, on rice plants against *Pyricularia oryzae* and on wheat plants against *Fusarium culmorum* and *Septoria nodorum* as well against phylum Nematoda. In the following tests, *Pseudomonas fluorescence* strain 197 from the All-Russian Microbiological Collection was used. Said bacterium is one of the bacterial strains isolated from the root hairs of wheat plant in a field of one of the farms at Odintsovo district in Moscow region.

Although MF3 is from an exact microbial strain it is to be considered that related active proteins can be produced also by other organisms, and those proteins are covered by the present invention. Whereas MF3 sequence resembles a known enzyme structure, the enzymatic activity is not necessarily required for said biological activity of MF3. On the contrary, because MF3 can be subjected to specific proteolysis, or boiled with retaining of said activity, it is more likely that other biological properties of MF3 are the origin of the plant protection.

The invention is further illustrated but not limited by the following examples of specific embodiments of the invention.

EXAMPLE 1

Cultural and Morphological Properties of *Pseudomonas* Fluorescence Strain 197

The isolate is cultivated on synthetic culture medium (King's B medium) containing 20 g/l peptone, 2.5 g/l $K_2HPO_4$, 6 g/l $MgSO_4$, 20 g/l sucrose. During 18-h incubation at 28° C. on agar culture medium bacterium forms small (1.5-2 mm) spherical colonies with entire margin and opaque, mat surface. After 18-h incubation at 28° C. in liquid medium with shaking, bacterial titer is $10^{10}$ cells/ml. Bacterium produces greenish-yellow transparent and diffusible fluorescent pigment. The cells are gram-negative, short, small non-fastidious motile rods with flagella. Optimal temperature of growth of the strain 197 is 28° C., minimum is 4° C. and maximum 43° C. Optimal pH is around 7.0. Bacterium does not fix atmospheric nitrogen and does not use compounds with one carbon atom as the source of carbon. Source of carbon for bacterium is sucrose, glucose, glycerin and/or other substances containing more than one carbon atom. Bacterium is a chemo-organotroph, aerobe, oxidase- and catalase-positive organism. Metabolism is respiratory and not fermentative. Data of the morphological cultural physiological and biochemical analysis permitted us to conclude that isolated bacterial strain belongs to *Pseudomonas fluorescence* species (Cion, 1948; The shorter Bergey's manual of determinative bacteriology, 1980).

After cultivation in optimal conditions (see above), the bacterial cells were collected by centrifugation at 6000 rpm during 15 min at room temperature (Sorvall-RC28S centrifuge, rotor GS-3) and washed twice with distilled water. The material was re-suspended in 50 mM potassium-phosphate buffer, pH 7.0, containing 1 mM EDTA to give the final concentration of $4\text{-}5 \times 10^{10}$ cells per ml. The suspension was heated in a boiling water bath for 20 min and centrifuged for 15 min at 6000 g to remove the bacterial cells and cell debris. Supernatant was treated sequentially with 1 volume (w/v) of cold chloroform and 2 volumes (w/v) of cold propanol. Precipitate was removed by centrifugation for 15 min at 6000 g. Supernatant was mixed with cold propanol in such a way that the final concentration of propanol was 5 volumes. Precipitate was collected by 20-min centrifugation at 10000 g, then dissolved in 0.1 M Tris-HCl buffer (pH 7.0) containing 0.1 M NaCl, 1 mM EDTA, and 1% Triton X-100. The resulting material was thereafter heated for 2 min in a boiling water bath and after cooling applied on a Sephadex G-50 column (1.2×90 cm), previously equilibrated with the same buffer. Active fractions were pooled, evaporated and precipitated by 5 volumes of cold ethanol. The next step of purification was vertical polyacrylamide gel electrophoresis (PAGE) described by Laemmli (1970) except that the separating gel and buffer had Triton X-100 instead of sodium dodecyl sulphate. It was used 20% polyacrylamide containing 0.1% Triton X-100. Elution of active bands was made by resumption of gel electrophoresis. To make the protein bands visible, the gel was stained with Coomassie Brilliant Blue R-250. The amount of protein was determined by the method of Bradford (1976) with bovine serum albumin as the standard.

The following examples serve to illustrate certain aspects of the present invention. A purified boiled extract of the *P. fluorescence* strain 197 was used in these experiments. It

EXAMPLE 2

Protective Properties of MF3 Against Tobacco Mosaic Virus (TMV) of Tobacco Plants should be noted that the preparation can be also obtained from genetically engineered producer organisms, like *E. coli* described here later on.

All the microbial, nematode and plant strains and varieties were from the culture collection of the Research Institute of Phytopathology, Golitsino, Moscow region, Russia.

Tobacco plants (*Nicotiana tabacum* var. *Virginia* and *Nicotiana glutinosa*) were grown to the stage of six leaves (for about 3 weeks) in pots with soil in a climatic chamber at relative humidity (RH) of 60% and temperature of 24° C. with equal light and dark periods (12 h each). Leaves of tobacco plants were inoculated with a paintbrush using carborundum as an abrasive. Each half of a tobacco leaf of 3-week-old plants was rubbed with carborundum with 50 µl of extract of *P. fluorescence*. For control, plant leaves were treated with the same volume of buffer. Two days later, the same leaves were rubbed with a Tobacco Mosaic Virus suspension (0.3 µg/ml, in 10 mM K-phosphate buffer, pH 7.0; 0.3 ml/half of leaf). The amount of infective lesions on each half leaf was estimated after 3 days. Development of the disease was measured as a ratio of number of lesions in test to control. The results are shown in Table I. The purified extract from *P. fluorescence* shows a protective effect on tobacco plants from TMV-infection.

TABLE I

Antiviral activity of MF3 on tobacco plants

| Tobacco variety | Number of lesions/control | | |
|---|---|---|---|
| | 1-st leaf | 2-nd leaf | 3-rd leaf |
| *N. glutinosa* | 0/9 | 0/41 | 1/10 |
| *N. tabacum* var. *Virginia* | 0/63 | 0/106 | 0/29 |

EXAMPLE 3

The Systemic Nature of MF3 Activity Against Tobacco Mosaic Virus (TMV) on Tobacco Plants Tobacco plants (*Nicotiana tabacum* var. *Virginia* and *Nicotiana glutinosa*) were grown to the stage of six leaves (for about 3 weeks) in pots with soil in a climatic chamber at RH 60% and temperature of 24° C. with equal light and dark periods (12 h each). Two lower leaves of plants were rubbed (with carborundum) with 50 µl of MF3 solution. Two days later the same and upper leaves were inoculated with TMV suspension. In control, leaves were treated with buffer. The results are presented in Table II.

TABLE II

Number of lesions on leaves of whole tested tobacco plants pretreated by MF3 solution. Systemic antiviral activity of MF3 is shown.

| | Lower leaves were treated with MF3 | | | Lower leaves were treated with buffer | | |
|---|---|---|---|---|---|---|
| Tobacco plants | n. 1 | n. 2 | n. 3 | n. 4 | n. 5 | n. 6 |
| Upper leaves | 0 | 1 | 0 | 570 | 585 | 388 |
| Lower leaves | 4 | 3 | 0 | 270 | 185 | 43 |

EXAMPLE 4

Activity of MF3 Against *Pyricularia oryzae* on Rice Plants

A natural isolate H-5-3 of *Pyricularia oryzae* Cav. was used. The fungus was cultured at 28° C. on agar minimal medium containing 3 mg/ml casein hydrolyzate (Sigma). Spores (conidia) from 10-day-old culture were washed with distilled water (4° C.). Mycelial impurities were removed by filtration through Miracloth (Calbiochem-Boehring Corp.) and through two layers of a stainless steel net (pore size 50 µm). The spore suspension was washed by double centrifugation for 15 min at 7000 g and re-suspended in distilled water. The spore concentration was counted in a hemocytometer under microscope.

Rice *Oryza sativa* L. of cv. Sha-tiao-tsao susceptible to the above-mentioned strain of fungus was used. Plants were grown up to a stage of four leaves (about 13-15 days) in pots with soil in a climate chamber at RH 95% and temperatures of 30° C. and 23° C. during the light and dark periods of 12 h each. The light source (20 klux) was 10 kW xenon lamp (DKsT-10000) with a water filter.

Rice plants were sprayed by spore suspension (100,000 spores/ml, 5 ml of suspension per one pot). Treated plants were incubated during 18-24 h in a moist chamber in the dark at 23° C. and then placed under the light at a climate chamber to observe disease symptoms for 10 days. To test the inoculum's viability, drops of the spore suspension were incubated for 15 h in a multi-well microtiter plate in the dark at 23° C. The germination of spores was then counted. The buffer solutions of MF3 preparations were added into the spore inoculum. Control samples contained equal volume of the buffer.

All MF3 preparations at the used concentrations did not inhibit germination of *P. oryzae* spores in water. However, addition of the preparations to the inoculum protected the rice plants from the blast disease to a marked degree.

TABLE III

Antiblast activity of different bacterial *Pseudomonas* preparations.

| Bacterial preparation | Protein (µg/ml) | Number of plants (unit) | Type of infection quantity of lesions × type* | Disease** development (%) |
|---|---|---|---|---|
| Boiled extract | 90 | 22 | 1 × 0; 10 × 0.1; 3 × 1; 8 × 2 | 30 |
| Propanol precipitate | 50 | 24 | 17 × 0.1; 3 × 1 | 6.5 |
| | 20 | 26 | 1 × 01; 1 × 2; 1 × 0.1; 1 × 2; | 9.1 |
| | 5 | 25 | 1 × 0.1; 2 × 1; 12 × 1; 2 × 3 | 27 |
| Fractions from Sephadex G-50 column | 3 | 22 | 5 × 1; 10 × 0.1; 2 × 2 | 15 |
| Control | 0 | 23 | 1 × 0.1; 4 × 1; 13 × 2; 5 × 3 | 70 |

*Type of infection was determined according to the method of Latterel et al., 1964.
**Disease development was calculated by formula:

$$R = \frac{(a \times b) \times 100}{N \times 3}$$

R - disease development (%);
a - quantity of infected plants;
b - type of infection;
N - total quantity of plants;
3 - high type of infection.

EXAMPLE 5

Activity of MF3 Against *Septoria nodorum* on Wheat Plants

A natural isolate of *Septoria nodorum* was used. Plants of wheat (Mironovskaya 808) were grown up to a stage of two leaves (about 13-15 days) in pots with soil in a climate chamber.

Detached leaves of wheat were placed on Petri dishes (2% agar with 40 mg/l benzimidazol). On up place of each leaves, 5 μl of MF3 (concentrations: 1.25 mg/ml and 2.5 mg/ml) and on down place of each leaves 5 μl of buffer (for control) were dripped. After two days, all water drops were removed with a sterile cloth from leave surfaces and dripped with 5 μl of a spore suspension ($10^6$ ml). Petri dishes were placed in a dark room for 1 day and thereafter under a 10 kW xenon lamp (DKsT-10000) at 8-10 klux at the temperatures of 20-22° C. with the light period of 16 h. Symptoms were analyzed after 7 days.

TABLE IV

MF3 activity against *Septoria nodorum* on detached leaves of wheat.

| Control/experiment | Protein (mg/ml) | Degree of disease, (scores) | Inhibition of disease, (%) |
|---|---|---|---|
| Experiment-1 | 1.25 | 0.9 | 69.2 ± 16 |
| Control-1 | 0.0 | 3.1 | 0.0 |
| Experiment-2 | 2.5 | 1.2 | 59.2 ± 13 |
| Control-2 | 0.0 | 3.2 | 0.0 |

As shown by the results in Table IV, MF3 protected the leaves of wheat plants from *Septoria nodorum* disease to a marked degree.

EXAMPLE 6

Inoculation of Wheat Seeds by Bacteria with *Fusarium culmorum* (W. G. Sm) Sacc. and for the Stimulation of Plant Growth Pathogenic inoculum was obtained from 10-day-old cultures of two isolates of *F. culmorum*, which were grown on potato-dextrose agar. Concentration of the conidia in suspension was approximately $2 \times 10^6$ per ml. The test plant was wheat variety Mironovskaya 808. Treatment of wheat seeds with the suspension of *Pseudomonas fluorescence* strain (st. 197) cells or with the purified extract of bacterial strain protected wheat germ against *F. culmorum* causing root rot of wheat under mixed inoculation on rolls of germination paper in laboratory experiments (see details below).

The bacteria were cultivated on the following medium: 2 g of casein hydrolyzate, 10 g of sucrose, 3 g of yeast extract, 2.5 g $NaNO_3$, 0.5 g $MgSO_4\ 7H_2O$, 1 g $KH_2PO_4$, 20 g of agar per liter of distilled water. The bacteria were used in the test experiment on the 6th day of cultivation. Concentration of cells in the used suspensions was $10^7$-$10^8$ per ml.

Winter wheat seeds were surface-sterilized in 96% ethanol for 1 min, then soaked in sterile water, placed on Petri dishes, moistened, and incubated for 24 h at 23-24° C. Then germinated seeds were transferred onto other Petri dishes (30 seeds per a dish) and moistened with suspensions of conidia of *F. culmorum* and/or cells of strain 197. Total volume of suspension was 10 ml/dish (5 ml of spore suspension of *F. culmorum* and 5 ml of cell suspension of cells of st. 197 under mixed inoculation or 5 ml of one of these suspensions and 5 ml of sterile water under separate inoculation). After a 24-h incubation, the seeds were placed between two pieces (16×85 and 6×85 cm) of a dry germination paper (30 seeds on a pair of pieces), which were then covered by sterile polyethylene piece (6×90 cm) and rolled up. Three rolls/replications were used in each treatment. The rolls were placed in separate vessels, watered and incubated in the dark at 22-23° C. for 6 days, then placed on a laboratory table and incubated at 19-20° C. with 12-h daylight period for 6 days. The rolls were watered when the paper became dry. After this, the number of germinated seeds, the length of shoots and longest of roots and the dry weight were determined.

TABLE V

The number of germinated seeds, and the lengths of shoots, roots and dry weight under separate and mixed inoculation with *F. culmorum* and strain 197.

| Treatment (number of bacteria) | Number of germinated seeds | Length (cm) | | Dry weight (mg) | |
|---|---|---|---|---|---|
| | | Shoot | Roots | Shoot | Roots |
| Control | 25.7 | 15.5 | 16.1 | 9.2 | 6.2 |
| *F. culmorum* | 17.0 | 10.4 | 12.8 | 5.8 | 4.3 |
| *F. culmorum*+ +st.-197($10^7$) | 17.7 | 12.9 | 15.5 | 7.7 | 5.4 |
| *F. culmorum*+ +str.197($10^8$) | 18.3 | 12.7 | 15.0 | 7.1 | 5.1 |
| Str.197($10^8$) | 28.7 | 16.0 | 17.1 | 9.6 | 7.1 |
| LSD 0.05* | 2.0 | 0.8 | 0.9 | 1.0 | 0.5 |

*LSD—Least Significant Difference

The analysis of the data in Table V showed that strain 197 significantly reduced the development of the disease. The shoot length was 22-23%, maximal roots length 18-21%, dry weight of shoots 22-23%, and the dry weight of roots 19-26% higher under mixed inoculation than under inoculation by *F. culmorum*. There were no significant differences between treatments with the bacterium in concentrations $10^7$-$10^8$ cells/ml under mixed inoculation.

The bacteria were cultivated in a liquid medium containing 20 g of peptone, 2.5 g $KH_2PO_4$, 6 g $MgSO_4 \times 7H_2O$, 20 g of sucrose per liter of distilled water. The bacteria were used in experiment on the second day of the cultivation. Concentration of the cells in suspension was approximately $10^{10}$ per ml.

MF3 was prepared by the following method: the bacterial cells were washed twice by water, suspended in 10 mM sodium phosphate buffer (pH 7.5) in cell concentration which was more than 10 times higher than in the culture medium. Then the suspension was boiled in water bath for 30 min. Cells debris was separated by centrifugation. The supernatant was used in the experiment. Before application, the extract was diluted by 15 times.

Non-sterile wheat seeds were placed in shallow vessels (90 seeds for vessel) and dipped in 5 ml portions of cell suspension, or in cell extract of *Pseudomonas fluorescence*, or in sterile water, and incubated at 20° C. for 5 h. Thereafter 5-ml portions of spore suspension of *F. culmorum* ($2 \times 10^6$ spores/ml) or 5 ml of sterile water were added into the vessels in different studies. After a 24-h incubation in the vessels, the seeds were placed between two pieces (16×85 cm and 6×85 cm) of dry germinating paper (30 seeds on a pair of piece), which were then covered by sterile polyethylene piece (6×90 cm) and rolled up. Three rolls/replications were used in each experiment. Then the rolls were incubated in the same conditions as in the previous experiment.

Number of germinated seeds, shoots and maximal roots length and dry weights were determined (Table VI).

TABLE VI

Number of germinated seeds, shoots, root lengths, and dry weights under separate and mixed inoculation with *F. culmorum* and *Pseudomonas fluorescence* (str.197) cell suspension, or its extract.

| Treatment | Number of germinated seeds | Length (cm) Shoot | Length (cm) Roots | Dry weight (mg) Shoot | Dry weight (mg) Roots |
|---|---|---|---|---|---|
| Control | 25.0 | 16.1 | 17.2 | 11.5 | 5.5 |
| F. culmorum | 18.7 | 10.3 | 12.2 | 5.9 | 3.0 |
| F. culmorum+MF3 | 18.0 | 12.1 | 14.3 | 7.3 | 3.7 |
| F. culmorum++Str.197 | 18.7 | 12.2 | 13.0 | 7.3 | 3.4 |
| MF3 | 24.3 | 17.2 | 17.2 | 12.5 | 5.7 |
| str.197 | 25.3 | 18.5 | 18.6 | 14.1 | 5.7 |
| LSD 0.05 | 4.4 | 0.8 | 1.1 | 1.0 | 0.6 |

The shoot length was 17.3-18.6%, maximal roots length 6.6-17.4%, dry weight of shoots 23.1-23.6%, and dry weight of roots 12.3-24.3% higher under mixed inoculation than under inoculation by *F. culmorum*. The shoot length and the weight of germs, treated with the cell suspension, were, respectively, 14.7% and 22.0% higher than in control.

EXAMPLE 7

Protective Activity of MF3 Against Potato Late Blight Disease

A natural isolate of *Phytophtora infestans* and potato variety "Lorch" were used in the test experiment. To investigate the influence of treatment with str. 197 bacterial preparation to *Ph. infestans* infection process, potato tubers were moistened by bacterial suspension ($10^7$ cells/ml). After 7-10 days these tubers were planted into a greenhouse. Leaves of the plants obtained were cut and inoculated with a virulent race of *Ph. infestans* for determination of the penetration intensity, lesion growth rate, intensity of sporulation, and tuber colonization rate. Detached leaves obtained from non-treated potato tubers were used as the control.

Penetration intensity was measured by inoculation of the lower side of detached potato leaves by spraying with a *Ph. infestans* spore suspension ($10^3$ spores/ml) with a subsequent incubation in a moist chamber for 2-3 days at 18-20° C. Then the number of lesions per cm² of leaf surface were estimated. The results of a typical experiment are presented in Table VII.

TABLE VII

Amount of lesions of leaf surface of potato plants, treated with MF3.

| | Amount of lesions per cm² of leaf surface | | | | | m ± (P = 0.95) |
|---|---|---|---|---|---|---|
| Leaves from untreated plants | 6.5 | 9.2 | 6.7 | 7.1 | 10.3 | 8.0 ± 2.1 |
| Leaves from plants treated with MF3 | 1.4 | 3.3 | 2.6 | 1.5 | 3.0 | 2.4 ± 1.1 |

Lower sides of detached potato leaves were inoculated by single drops of *Ph. infestans* spore suspension (about $10^3$ spores/ml). Lesion growth rate was determined by measuring the diameter of lesions at 4th or 5th days after inoculation. The results are shown in Table VIII.

TABLE VIII

Diameter of lesions formed by *Ph. infestans* on potato leaves in plants untreated or treated with MF3.

| Source of sample | Diameter of lesions (mm) on leaves | | | | | m ± (P = 0.95) |
|---|---|---|---|---|---|---|
| Leaves from untreated plants | 39 | 41 | 38 | 43 | 37 | 39.6 ± 5.4 |
| Leaves from plants treated with MF3 | 5 | 4 | 6 | 5 | 3 | 4.6 ± 2.9 |

Intensity of sporulation was determined by calculating the amount of spores produced by single lesion. Inoculation was carried out with drops of *Ph. infestans* spore suspension as it was described before in Example 7. After 5 days, spores were washed off from certain number of lesions on leaf surface, and the quantity of the spores per one lesion was counted. The results of these experiments are shown in Table IX.

TABLE IX

Amount of *Ph. infestans* spores ($10^3$) per lesion on potato leaves from plants, which were treated with MF3.

| Source of sample | Amount of *Ph. infestans* spores (×103) per lesion on potato leaves | | | | | M ± (P = 0.95) |
|---|---|---|---|---|---|---|
| Leaves from untreated plants | 185 | 209 | 216 | 174 | 182 | 193 ± 23 |
| Leaves from plants treated with MF3 | 43 | 56 | 36 | 52 | 49 | 47 ± 10 |

Effects of treatment of potato tubers with MF3 were determined by estimating the tuber colonization rate. Potato tubers were moistened by bacterial suspension ($10^7$ cells/ml). After 7-10 days, pieces with sizes 0.5×0.5×5 cm were cut from the tubers. One of these tuber pieces was inoculated by *Ph. infestans* spores. Then potato pieces were placed in a moisture chamber and incubated at 18-20° C. The length of the pathogen-colonized part of each tuber slice was measured after 8-9 days. The results of these experiments are shown in Table X.

TABLE X

Length of the colonized part of potato slices treated with MF3 and then inoculated with *Ph. infestans*.

| Source of sample | Length of the colonized part of potato tuber pieces (mm) | | | | | m ± (P = 0.95) |
|---|---|---|---|---|---|---|
| Slices from untreated tubers | 19 | 21 | 22 | 21 | 20.5 | 20.7 ± 1.4 |
| Slices from tubers treated with MF3 | 18 | 16.5 | 20 | 15.5 | 19 | 17.8 ± 2.3 |

Determination of disease development on potato tubers when treated with MF3 was performed as follows: Potato tubers were moistened by bacterial preparation ($10^7$ cells/ml). After 7-10 days such tubers were planted with routine techniques in plots of 2.8×9 m. These plots located in a large potato field. Distances between the experimental plots were above 1 m. There was a natural infection background. Tubers, which were harvested from the experimental plots which were treated by MF3, were damaged by *Ph. infestans* only 15% while tubers from the control area were damaged 27%.

In other experiments, untreated potato tubers were planted in plots of 2.8×7.0 m. These plants were sprayed with bacterial suspension (concentration $10^4$ cells/ml) with dose of 400 l/hectare, 4 times with appropriate time intervals during the vegetation period. In these experiments, a disease-susceptible potato variety "Lorch" was used. During the vegetation period, testing of disease development was performed at 10-day intervals. After the end of vegetation period each of the plots was divided in 5-6 parts with area of about 10-15 m². The degree of damage in potato tubers was determined on each of these subplots. Plants of control plots were not treated by bacterial suspension. Tubers, which were harvested from plots treated with strain 197, were damaged with *Ph. infestance* only by 11% while the tubers from control plots were damaged by 27%.

EXAMPLE 8

Influence of MF3 on Colorado Beetle Larvae

Colorado beetle larvae were grown from eggs (collected from ARRIP fields with potato) on potato leaves saved in glass with water. For experiment, potato leaves (cv. Sante) were taken from plants grown in the field (from 40-50 days old plants).

This experiment was conducted with 2nd stage larvae. Cuttings from leaves (16 mm) were dipped into MF3 solution or water (control). After drying the cuttings were transferred onto a wet paper on a Petri dish and 3 larvae were put on it. After 24 hours, cuttings were dried and the areas, which were eaten by larvae were calculated. Each experiment was performed three times (Table XI).

TABLE XI

|  | Total area eaten by larvae | |
| --- | --- | --- |
|  | Sq. Mm | % of control |
| Control | 108.5 | 100 |
| Buffer | 79.0 | 72.8 |
| 0.01 mg/l MF3 | 62.5 | 57.6 |
| 0.1 mg/l MF3 | 35.0 | 32.3 |

For this experiment with 4th stage larvae cuttings size was increased (diameter 36 mm) and for each cutting one larvae was used. Results are presented in table XII,

TABLE XII

|  | Total area eaten by larvae | |
| --- | --- | --- |
|  | Square mm | % of control |
| Control | 263.3 | 100 |
| Buffer | 347.7 | 132.0 |
| 0.01 mg/l MF3 | 178.0 | 67.6 |
| 0.1 mg/l MF3 | 181.3 | 68.9 |

EXAMPLE 9

Resistance of Tested Transgenic Potato Plants to *Erwinia carotovora*

The ability of *E. carotovora* to macerate plant tissues indicates its typical pectolytic activity. However, this does not prove pathogenicity of the bacterium in natural environments. False positive results are due to naturally occurring endophytic or epiphytic microorganisms associated with inoculated tissue. Disinfect the surface of the tissue by immersing in a 10% household bleach agent (5.25% of sodium hypochlorite), solution for 10 min and air-dry. Repeat bleach treatment or sterilize with alcohol flame. Cut the tissue into convenient pieces, place on a Petri dish on moist sterile filter paper and inoculate with 0.1-1 ml of the bacterial suspension (ca. $10^6$ CFU/ml) from a 24-h-old culture. Incubate at 20-27° C. for 48 h and probe the tissue around the inoculation site with a spatula or needle to determine whether decay and tissue maceration have occurred.

TABLE XIII

| Resistance of tested transgenic potato tubers to *Erwinia carotovora*. | |
| --- | --- |
| transgenic plant line | Size of necrotic lesion (mm) |
| Nevskiy, non-transgenic | 21.9 |
| N53 | 14.1 |
| N 56 | 6.9 |
| N 71 | 9.4 |
| LSD0.05 | 3.5 |

Table XIII shows that transgenic potato lines numbers N53, N56, and N71 show resistance to *Erwinia carotovora*.

EXAMPLE 10

Resistance of Transgenic Potato Plants to the Late Blight Disease Causal Agent, *Phlytophthora infestans*

Laboratory tests were carried out on detached leaves of MF3-expressing transgenic potato cultivars inoculated with the Moscow region population of *Ph. infestans* and simultaneously on leaves of non-transgenic plants belonging to the same cultivars inoculated with the same isolate of the pathogen. Ten leaves from every cultivar were inoculated by spraying of a zoospore suspension (5-6 zoospores in the visual field of microscope at magnification ×120). After inoculation, the leaves were incubated for 12 h at 18° C. in a moist chamber. After 3 days, the number of necroses per $cm^2$ of leave cover was counted. The leaves were inoculated with 8-µl drops of zoospore suspension (1-2 drops per leaf). Zoospore concentration was the same as in Example 1. Inoculated leaves were incubated in a moist chamber in dark during 18 h. After this the residuals of suspension were removed by filter paper and leaves were put into a moist chamber at 20° C. After 5-6 days, the lesion area ($mm^2$) and the sporulation capacity were measured (within a 4-score scale).

The model used provides measures for dynamics of disease during vegetation season and then calculates corresponding harvest losses (eq 1):

$$W = \frac{S}{q} 100, \text{ wherein,} \quad (eq\ 1)$$

W—harvest loss (%)

S—area under the curve, which describes the increase of ratio of plant infection (AUDPC);

q—elongation of the period from formation of inflorescence to the end of vegetation of non-blighted potato (days).

The "mean q" is determined by the early ripeness of the potato cultivar and by the conditions of its planting. Average "mean q" for different groups of early ripeness is 46 days for early- and middle-early cultivars, 52 days for middle early cultivars, 84 days for middle late cultivars, and 97 days for late cultivars. The calculations are conducted by means of a software or nomogram (FIG. 1) for potato cultivars of 3 groups of potato cultivars (early, middle and late).

The nomogram of FIG. 1 includes the following scales:

A—lesion index (number of necroses magnified by their size), in fraction of the standard;

I—incubation period, in fraction of the standard;

S—sporulation capacity, in fraction of the standard;

P—potential losses of potato harvest from late blight because of premature dying off of leaves (%).

Scale P is represented by three parts for late (L), middle (M), and early (E) potato cultivars.

The following scale can be used for estimation of cultivar resistance to the late blight disease:

| | |
|---|---|
| Harvest losses <5%: | Resistant cultivar (R), |
| Harvest losses - 5-15%: | Moderately resistant cultivar (MR), |
| Harvest losses - 16-35%: | Moderately susceptible cultivar (MS), |
| Harvest losses >35%: | Susceptible cultivar (S), |

A natural isolate of *Ph. infestans*, common in Moscow area, and transgenic potato plant lines expressing MF3 were used. Non-transgenic cultivar Nevsky served as the control. Tables XIV and XV show results of the laboratory tests. Table XVI shows the results of the field tests.

TABLE XIV

Resistance of transgenic potato plants to the Moscow area population of the late blight disease causal agent *Phytophthora infestans*.

| Number of plant line | Inoculation efficiency, number of necroses/cm2 | d-necrotic lesion size, (mm) | Sporulation capacity, (scores) | Index of resistance | Crop losses, (%) | Level of resistance* |
|---|---|---|---|---|---|---|
| Control | 0.36 | 22.3 | 4 | 4 | 33 | MS |
| N 21 | 0.14 | 7.4 | 20.1 | 4 | 26 | MS |
| N 24 | 0.11 | 20.6 | 2.5 | 4 | 24 | MS |
| N 34 | 0.05 | 2.9 | 0.01 | 8 | 0 | R |
| N 55 | 0.01 | 5.1 | 0.01 | 8 | 0 | R |
| N 53 | 0.02 | 20.7 | 2.6 | 5 | 18 | MS |
| N 56 | 0.21 | 1.9 | 0.01 | 8 | 0 | R |
| N 71 | 0.08 | 1.2 | 0.01 | 8 | 0 | R |
| LSD0.05 | 0.08 | 1.3 | 0.2 | | 3.7 | |

*Correlated to the Index of resistance scale (from 1 to 9) as follows: 8-9 = R; 7-6 = MR; 5-4 = MS; 1-3 = S)

TABLE XV

Resistance of tested transgenic potato plants to the Sakhalin population of the late blight disease.

| Number of transgenic plant lines | Inoculation efficiency number of necroses/cm2 | d-necrotic lesion size, mm | Sporulation capacity, scores | Index of resistanse | Crop losses, % | Level of resistance |
|---|---|---|---|---|---|---|
| Control | 0.1 | 14.8 | 4 | 4 | 2 | MS |
| N21 | 0.01 | 7.4 | 0.8 | 6.5 | 7 | MR |
| N24 | 0.01 | 1 | 0.01 | 8 | 0 | R |
| N34 | 0.02 | 9.5 | 0.8 | 6 | 9 | MR |
| N55 | 0.01 | 1 | 0.01 | 8 | 0 | R |
| N53 | 0.05 | 2.6 | 0.01 | 6 | 9 | MR |
| N56 | 0.1 | 1 | 0.01 | 8 | 0 | R |
| N71 | 0.1 | 1.7 | 0.01 | 8 | 0 | R |
| LSD 0.05 | 0.03 | 1.9 | 3.4 | | 2 | |

TABLE XVI

Resistance of transgenic potato plants to the late blight disease under natural infections conditions in the field.

| | *Disease development (%) | | | | | | |
|---|---|---|---|---|---|---|---|
| transgenic plant line | 31.07.00 | 3.08.00 | 7.08.00 | 14.08.00 | 21.08.00 | 28.08.00 | S** |
| Control | 0.1 | 0.5 | 5 | 10 | 25 | 80 | 4.5 |
| N24 | 0 | 0.1 | 5 | 7 | 15 | 80 | 3.6 |
| N34 | 0 | 0.1 | 2 | 10 | 20 | 60 | 3.3 |
| N55 | 0.1 | 0.5 | 3 | 5 | 10 | 55 | 2.3 |
| N53 | 0 | 0.1 | 0.9 | 3 | 4 | 65 | 1.8 |

TABLE XVI-continued

Resistance of transgenic potato plants to the late blight disease under natural infections conditions in the field.

| transgenic plant line | *Disease development (%) | | | | | | |
|---|---|---|---|---|---|---|---|
| | 31.07.00 | 3.08.00 | 7.08.00 | 14.08.00 | 21.08.00 | 28.08.00 | S** |
| N56 | 0 | 0 | 0 | 1.5 | 3 | 45 | 1.1 |
| N71 | 0 | 0 | 0 | 1 | 2 | 50 | 1.0 |
| LSD 0.05 | | | | | | | 0.9 |

*the numbers in boxes below refer to the dates of testing (day, month, year)
**S = area under the curve which describes the increase of ratio of plant infection (AUDPC).

EXAMPLE 11

Resistance of Tested Transgenic Potato Plants to the Potato Cyst Nematode *Globodera rostochiensis* Ro1-Type Pot Experiment Cysts of *Globodera rostochiensis* Ro1-type were obtained from soil of Agricultural experimental station of All-Russian Potato Research Institute, Korenevo, Moscow region. Transgenic potato plants with mf3-gene were used.

Cysts of *Globodera rostochiensis* (5000 eggs/100 ml soil) were used for inoculation of soil in 300-ml plastic pots. At the same time, 1 tuber of the transgenic potato was planted in each pot. After 2.5-3 months calculations of cyst number on each plant were determined (Table XVII).

TABLE XVII

The number of *Globodera rostochiensis* cysts collected from transgenic potato plants (P = 0.90).

| Number of transgenic plant lines | number of cysts per plant |
|---|---|
| Nevskiy nontransgenic | 290 |
| N 53 | 241 |
| N 56 | 259 |
| N 71 | 332 |
| LSD 0.10 | 38 |

Number of cysts collected from transgenic line N53 was considerably less than from control non-transgenic plants.

EXAMPLE 12

Resistance of Tested Transgenic Potato Plants to the Potato Cyst Nematodes *Globodera rostochiensis* Ro1-Type Field Experiment Cysts of *Globodera rostochiensis* Ro1-type were obtained from soil of Agricultural experimental station of All-Russian Potato Research Institute, Korenevo, Moscow region. Transgenic potato plants with mf3-gen were used. Tubers of each line of transgenic potato were planted in soil of Agricultural experimental station of All-Russian Potato Research Institute, Korenevo, Moscow region (4816 juveniles of *Globodera rostochiensis* Ro1-type/100 ml of soil). Plants were harvested on 12 Aug. 2002 and the number of cysts on each plant's roots were determined (P=0.90).

TABLE XVIII

The number of *Globodera rostochiensis* cysts collected from roots of transgenic potato plants (field experiment).

| Number of transgenic plant lines | number of cysts per plant |
|---|---|
| Nevskiy non-transgenic | 73 |
| N 53 | 63 |
| N 56 | 60 |
| N 71 | 56 |
| LSD0.10 | 9 |

The number of cysts collected from transgenic plants with mf3 gene, grown on the experimental field was less than from control non-transgenic plants. Particularly, the line N71 showed resistance. The number of cysts collected from this line was 27% less than from control.

EXAMPLE 13

Testing of Resistance of Tobacco Plant Transformants with mf3 Gene to Potato Virus X (PVX)

Fully infected plants of PVX was used as a source for leaf extract. The extract was stored frozen at −70° C. Four 3-weeks-old tobacco plants (transgenic or non-transgenic) were used for each plant variety. The third and fourth (counted from the top) leaves of the plants were inoculated with PVX.

One, 2, and 3 weeks after the inoculation, PVX was tested in all the treated leaves using standard enzyme-linked immuno-sorbent assay (ELISA) with a PVX ELISA kit (All-Russian Potato Research Institute, Korenevo, Moscow region). The absorbance using 0.1% leaf juice was measured according to the standard assay procedures described by the manufacturer. The results of these experiments are presented in Table XIX. These results show a high resistance of transgenic plants to PVX (mostly 90%).

TABLE XIX

Results of ELISA testing of tobacco plant transformants including mf3 gene construct to PVX.

| Transgenic plant lines | Absorption at 490 nm | | |
|---|---|---|---|
| | 1 week after inoculation | 2 week after inoculation | 3 week after inoculation |
| Positive control | 0.010 | 0.945 | 2.458 |
| Negative control | 0.008 | 0.010 | 0.010 |
| 12 | 0.034 | 0.013 | 1.522 |

TABLE XIX-continued

Results of ELISA testing of tobacco plant transformants including mf3 gene construct to PVX.

| Transgenic plant lines | Absorption at 490 nm | | |
|---|---|---|---|
| | 1 week after inoculation | 2 week after inoculation | 3 week after inoculation |
| 67 | 0.009 | 0.940 | 2.454 |
| 38 | 0.022 | 0.032 | 2.248 |
| 107 | 0.008 | 0.027 | 2.392 |
| 24 | 0.018 | 0.015 | 0.140 |
| 33 | 0.027 | 0.028 | 0.006 |
| 37 | 0.017 | 0.022 | 0.036 |
| 42 | 0.004 | 0.012 | 0.014 |
| 43 | 0.053 | 0.015 | 0.009 |
| 85 | 0.010 | 0.040 | 0.005 |
| 88 | 0.010 | 0.010 | 0.013 |
| 99 | 0.079 | 0.016 | 0.006 |
| 101 | 0.011 | 0.017 | 0.035 |
| 633 | 0.004 | 0.027 | 0.090 |
| 1 | 0.109 | 0.018 | 0.009 |
| 8 | 0.008 | 0.010 | 0.008 |
| 21 | 0.089 | 0.013 | 0.003 |
| 39 | 0.003 | 0.022 | 0.050 |
| 40 | 0.010 | 0.016 | 0.138 |
| 48 | 0.049 | 0.046 | 0.009 |
| 77 | 0.072 | 0.048 | 0.017 |
| 87 | 0.073 | 0.037 | 0.019 |
| 94 | 0.150 | 0.010 | 0.012 |
| 95 | 0.007 | 0.035 | 0.035 |
| 635 | 0.012 | 0.038 | 0.051 |
| 23 | 0.039 | 0.015 | 0.040 |
| 46 | 0.059 | 0.020 | 0.051 |
| 32 | 0.048 | 0.056 | 0.034 |
| 22 | 0.094 | 0.031 | 0.039 |
| 31 | 0.024 | 0.060 | 0.053 |
| 78 | 0.018 | 0.021 | 0.114 |
| 80 | 0.078 | 0.049 | 0.050 |
| 6 | 0.049 | 0.027 | 0.038 |
| 7 | 0.068 | 0.067 | 0.016 |
| 10 | 0.026 | 0.050 | 0.075 |
| 49 | 0.035 | 0.065 | 0.061 |
| 106 | 0.029 | 0.050 | 0.026 |
| 50 | 0.061 | 0.019 | 0.024 |
| 64 | 0.078 | 0.021 | 0.036 |
| 91 | 0.041 | 0.032 | 0.212 |
| 631 | 0.099 | 0.074 | 0.039 |

EXAMPLE 14

Testing of Tobacco Transformants with mf3 Gene to Tobacco Mosaic Virus (TMV)

The test procedures and materials were as in EXAMPLE 13. The results of these experiments are presented in Table XX. These results showed a high resistance to TMV in transgenic plants numbers 177, 152, 171 at 2 weeks and numbers 391, 286, 409, 279 at 3 weeks.

TABLE XX

Results of ELISA testing for the resistance of tobacco transformants including mf3 gene construct to TMV.

| Transgenic plant lines | Absorption at 490 nm | | |
|---|---|---|---|
| | 1 week after inoculation | 2 week after inoculation | 3 week after inoculation |
| Positive control | 0.104 | 2.078 | 2.276 |
| Negative control | 0.044 | 0.107 | 0.156 |
| 214 | 0.114 | 2.051 | 2.408 |
| 177 | 0.077 | 1.719 | 2.226 |

TABLE XX-continued

Results of ELISA testing for the resistance of tobacco transformants including mf3 gene construct to TMV.

| Transgenic plant lines | Absorption at 490 nm | | |
|---|---|---|---|
| | 1 week after inoculation | 2 week after inoculation | 3 week after inoculation |
| 152 | 0.108 | 1.267 | 2.305 |
| 232 | 0.153 | 1.965 | 2.574 |
| 173 | 0.163 | 2.201 | 2.424 |
| 148 | 0.168 | 2.333 | 2.426 |
| 226 | 0.110 | 2.011 | 2.460 |
| 171 | 0.099 | 0.727 | 2.223 |
| 183 | 0.136 | 2.162 | 2.474 |
| 400 | 0.056 | 1.897 | 2.350 |
| 391 | 0.043 | 0.077 | 0.153 |
| 286 | 0.051 | 0.089 | 0.374 |
| 409 | 0.090 | 0.124 | 0.422 |
| 279 | 0.047 | 0.093 | 0.153 |
| 233 | 0.334 | 2.450 | 2.474 |

EXAMPLE 15

Testing of Tobacco Plant Transformants with mf3 Gene to Potato Virus Y (PVY)

The test procedures and material were as in Example 12. The results of these experiments are presented in Table XXI. These results showed a high resistance to PVY 21 out of 27 (78%) transgenic plants lines.

TABLE XXI

Results of ELISA testing of tobacco plant transformants with mf3 gene construct to PVY.

| Transgenic plant lines | Absorption at 490 nm | | | |
|---|---|---|---|---|
| | 1 week after inoculation | 2 week after inoculation | 3 week after inoculation | 4 week after inoculation |
| Positive control | 0.058 | 1.940 | 1.804 | 1.663 |
| Negative control | 0.047 | 0.039 | 0.042 | 0.042 |
| 19 | 0.069 | 0.816 | 1.616 | 2.417 |
| 55 | 0.099 | 1.269 | 1.536 | 1.473 |
| 66 | 0.060 | 0.582 | 1.702 | 2.228 |
| 75 | 0.063 | 1.625 | 1.110 | 1.882 |
| 105 | 0.072 | 0.640 | 1.555 | 1.919 |
| 113 | 0.070 | 0.050 | 0.063 | 1.726 |
| 9 | 0.064 | 0.044 | 0.035 | 0.040 |
| 11 | 0.067 | 0.051 | 0.061 | 0.039 |
| 18 | 0.062 | 0.048 | 0.054 | 0.027 |
| 20 | 0.074 | 0.058 | 0.056 | 0.026 |
| 26 | 0.060 | 0.047 | 0.061 | 0.041 |
| 28 | 0.061 | 0.055 | 0.058 | 0.030 |
| 29 | 0.064 | 0.050 | 0.046 | 0.066 |
| 36 | 0.057 | 0.049 | 0.049 | 0.056 |
| 53 | 0.065 | 0.018 | 0.038 | 0.067 |
| 54 | 0.072 | 0.060 | 0.049 | 0.052 |
| 61 | 0.057 | 0.049 | 0.060 | 0.038 |
| 68 | 0.069 | 0.020 | 0.041 | 0.047 |
| 69 | 0.058 | 0.048 | 0.049 | 0.056 |
| 74 | 0.062 | 0.047 | 0.059 | 0.037 |
| 81 | 0.053 | 0.051 | 0.052 | 0.028 |
| 83 | 0.071 | 0.053 | 0.057 | 0.045 |
| 84 | 0.072 | 0.044 | 0.059 | 0.044 |
| 96 | 0.067 | 0.051 | 0.052 | 0.040 |
| 98 | 0.057 | 0.047 | 0.054 | 0.040 |
| 110 | 0.059 | 0.044 | 0.058 | 0.049 |
| 115 | 0.068 | 0.044 | 0.048 | 0.072 |

EXAMPLE 16

Testing of Resistance of Potato Transformants with mf3 Gene to Potato Virus X (PVX) Under Natural Infections Conditions (Table XXII)

TABLE XXII

Results of testing transgenic potato plants on PVX resistance under natural infection conditions.

| Transgenic plant lines | Absorption at 490 nm | | | |
|---|---|---|---|---|
| | Young growth | Before flowering | Flowering | Before harvest |
| Negative control | 0.014 ± 0.01 | 0.033 ± 0.02 | 0.067 ± 0.02 | 0.162 ± 0.01 |
| Positive control (Nevskiy non-transgenic) | 0.070 ± 0.06 | 0.545 ± 0.10 | 1.700 ± 0.14 | 2.480 ± 0.10 |
| N53 | 0.048 ± 0.05 | 0.480 ± 0.08 | 0.512 ± 0.05 | 2.146 ± 0.10 |
| N56 | 0.091 ± 0.03 | 0.477 ± 0.03 | 0.695 ± 0.05 | 2.442 ± 0.12 |
| N71 | 0.170 ± 0.01 | 0.378 ± 0.05 | 0.712 ± 0.08 | 0.822 ± 0.15 |
| Positive control (Lugovskoy non-transgenic) | 0.249 ± 0.01 | 0.807 ± 0.06 | 1.811 ± 0.07 | 2.423 ± 0.08 |
| L13 | 0.263 ± 0.03 | 0.346 ± 0.06 | 0.470 ± 0.06 | 2.364 ± 0.11 |
| L16 | 0.205 ± 0.02 | 0.335 ± 0.07 | 0.386 ± 0.05 | 0.792 ± 0.15 |

EXAMPLE 17

The Level of mf3 Gene Expression in Transgenic Lines

The monoclonal mouse antibodies to MF3 protein were sorbed onto the surface of a microtiter plate overnight at +4° C. and then rinsed three times with washing buffer (PBS buffer, 0.05% Tween® 20). 100 µl of plant juice diluted (1:100 and 1:10 w/v) in PBS buffer were added per well and incubated for 1 hour at 37° C., then rinsed for three times with washing buffer. 100 µl of monoclonal mouse antibodies to MF3 conjugated with horse-radish peroxidase (HRP) in concentration 5 µg ml$^{-1}$ were added per well and incubated for 1 hour at 37° C. Afterwards plate was rinsed three times with washing buffer followed by addition of substrate (3,3',5,5'-tetramethylbenzidine, TMB, Sigma). The reaction was stopped after 20 min by 2M HCl. The absorbance was measured according to instructions by Sigma Chem. Co, USA.

TABLE XXIII

ELISA results measured at 450 nm for transgenic lines (N 53, N 56, N 71).

| Line | Repetition | | | Simple average | Expression of mf3, pg/mg of tissue |
|---|---|---|---|---|---|
| | 1 | 2 | 3 | | |
| N Control | 0.002 | 0.006 | 0.002 | 0.004 | 0 |
| N 53 | 0.034 | 0.027 | 0.032 | 0.031 | 13 |
| N 56 | 0.030 | 0.032 | 0.034 | 0.032 | 13 |
| N 71 | 0.044 | 0.034 | 0.032 | 0.037 | 14 |

LSD 0.05 = 0.007

TABLE XXIV

ELISA results measured at 450 nm for transgenic lines (L 13, L16).

| Line | Repetition | | Simple average | Expression of mf3, pg/mg of tissue |
|---|---|---|---|---|
| | 1 | 2 | | |
| L Control | 0.028 | 0.027 | 0.027 | 0.0 |
| L 13 | 0.130 | 0.110 | 0.120 | 20.0 |
| L 16 | 0.058 | 0.052 | 0.055 | 10.0 |

LSD 0.05 = 0.027

LSD0.05=0.027

EXAMPLE 18

Protective Properties of MF3, Treated with Endopeptidases, Against Tobacco Mosaic Virus (TMV) of Leaves of Tobacco Plants In order to localize the elicitor activity of particular amino acid sequence of MF3 was subjected to peptidase cleavage. Endoproteinase Arg-C (sequencing grade from *Clostridium histolyticum*, Roche Molecular Biochemicals) was used 0.5 µg/assay for 24 h at 37° C. in a final volume of 50 µl of 0.1 M Tris-HCl, pH 7.6; 10 mM CaCl$_2$ (Christophe Breton et al, 2001). Digestion with Arg-C endoproteinase showed fragments with an activity related to intact MF3.

CNBr cleavage of MF3 was carried out in 100 µl of 70% (v/v) formic acid containing a few crystals of CNBr. The mixture was incubated in the dark for 24 h at room temperature under argon and was then stopped by adding 500 µl of water. The sample volume was reduced under vacuum, and formic acid was removed by solvent exchange with water (Christophe Breton et al, 2001). Chemical cleavage with CNBr showed fragments with an activity related to MF3.

Endoproteinase Lys-C (sequencing grade from *Lysobacter enzymogenes*, Roche Molecular Biochemicals) was used at 0.2 µg/assay in a final volume of 50 µl. The digestion was performed in 25 mM Tris-HCl, pH 8.5; 1 mM EDTA; 0.1% SDS at 37° C. for 16-24 h and stopped by addition of Laemmli buffer (Christophe Breton et al, 2001). Digestion with trypsin abolished antiviral activity of MF3.18.4 Trypsin digestion was performed in 0.5 M urea, 50 mM Tris-HCl, 1 mM CaCl$_2$ (pH 7.6) at 37° C. for 1 h and stopped by the addition of TCA to a 10% final concentration (according Promega manual). Digestion with trypsin abolished antiviral activity of MF3. Digestion of MF3 with trypsin and Lys-C abolished antiviral activity, whereas treatment with Endoproteinase Arg-C, CNBr and Endoproteinase showed a part of the MF3 protective properties. At least two amino acid sequences: 1-80 region and 105-149 region possess sequences, which could serve as a novel PAMP (pathogen-associated molecular pattern) that trigger the defense response in plants. Sequence alignment of homologous proteins from different sources (45 available sequences) shows regions: 29-85 and 105-149 to be conservative (alignment without gaps). It is probable that for antiviral activity the peptide with length of about 30 amino acids will be sufficient (inside the regions shown above). Hence the conservative regions are: 29-85 and 105-149

29-GA PLVYLQGAGN IIPGLEKALE GKAVGDDLEV
AVEPEDAYGE YAAELVSTLS RSMFE-85, (SEQ ID NO:3)

105-MQIVTI ADLDGDDVTV DGNHPLAGQR LNFKVKIVDI
RDASQEEIA-149. (SEQ ID NO:4)

EXAMPLE 19

Cloning and Sequencing of mf3 Gene

According to the N-terminal amino acid sequence, degenerate oligonucleotides were synthesized. High-molecular-weight chromosomal DNA was isolated from MF3 expressing cells and digested with 6 restrictases (BamHI, EcoRI, PstI, HindIII, SalI, SphI), separately and in pairs. Restriction products were separated according to molecular weights by agarose gel electrophoresis and transferred to HybondN-membrane by blotting procedure. Synthetic oligonucleotide was labeled by T4-polynucleotide kinase and [γ-32P] ATP and used as the radioactive probe in Southern hybridization experiments. Only one positive band per restriction appeared on the X-ray films. Based on molecular weights of positively hybridized fragments, the restriction map of antiviral protein chromosomal gene was constructed.

SalI digestion of chromosomal DNA was loaded on the 0.7% low-melting agarose and after electrophoresis DNA fragments approximately 3.3 kbp were isolated from the gel. They were further digested with HindIII and BamHI, loaded on the 1.0% low-gelling agarose gel and after electrophoresis DNA fragments approximately 0.7 kbp were isolated. They were ligated into vector pUC18 digested with HindIII and BamHI. Competent E. coli cells (strain XL1-blue) were transformed with this ligation mixture and were grown on LB-plates, containing ampicillin (70 mg/l). Colonies were transferred to the HybondN-membrane and subjected to colony hybridization procedure, using a radioactive oligonucleotide as the probe. About 70% of colonies showed positive hybridization.

Plasmid DNA from positive clone was isolated and used for sequencing of the insert. The DNA sequence coding N-end of antiviral protein appeared to be near BamH1 site. An open reading frame of 486 bp, starting with ATG and finished with TGA, was found. According to DNA coding region (SEQ ID NO: 2), the antiviral protein consists of 161 amino acid residues, as depicted in SEQ ID NO: 1. The procedures involved in the above cloning processes can be basically found in the handbook J. Sambrook, E. F. Fritsch and T. Maniatis, Molecular Cloning: A Laboratory Manual $2^{nd}$ ed. (Cold Spring Harbor, N.Y.: Cold Spring Harbor Laboratory Press) (1989).

EXAMPLE 20

Expression of mf3 in E. coli

To modify the ends of MF3 we used the plasmid DNA B/H4 as a template and the following primers: Nde-mf3 5'-GGAATTCCATATGCTGATCGCCGCC-3' (SEQ ID NO:5), Hind-mf3 5'-CCCAAGCTTAGTGGTGATGGC-CACC-3' (SEQ ID NO:6); the resulting fragment was digested with NdeI and HindIII and cloned into pGEMEX1 in place of gene 10. Reaction mixture (50 µl) consisted of approximately 10 ng of the template DNA, 1 uM each of primers, 0.2 mM of dNTP mixture, 1× Vent buffer (20 mM Tris-HCl, pH 8.8, 10 mM KCl, 2 mM MgSO₄, 10 mM (NH₄)₂SO₄, 0.1% Triton X-100) and 1 U Vent DNA polymerase (New England Biolabs). The thermal cycling program started with 5 min denaturing at 96° C., followed by 30 cycles of amplification: denaturing at 96° C. for 1 min, annealing at 45° C. for 1 min, and extension at 74° C. for 1 min; a final extension step was done for 10 min at 74° C.). PCR reaction samples (50 µl) were mixed with sample buffer and run on a 1% agarose gel containing 1 µg/ml ethidium bromide at 100 V for up to 1 h with Tris-borate EDTA as a running buffer. PCR product was eluted from 1% agarose gel with Prep-A-Gene DNA Purification Kit (Bio-Rad Laboratories) and recovered in 50 µl of 1×TE. Purified PCR product was digested with NdeI and HindIII and size fractionated on 1% agarose gel. DNA fragment about 500 bp was eluted with Prep-A-Gene DNA Purification Kit (Bio-Rad Laboratories) and recovered into 50 µl 1×TE.

The NdeI/AatII fragment of pGEMEX1 carrying ampicillin resistant gene, the AatII/HindIII fragment of pGEMEX1 containing the gene10 terminator of the bacteriophage T7, and the mf3 modified PCR product were combined by triple ligation to yield a plasmid pMF that contains the modified mf3 gene under the control of the gene10 promoter and terminator of the bacteriophage T7. Ligation mixture (5 µl) was transformed into competent E. coli strain XL1-blue (Stratagene). Transformants growing on LB-agar with ampicillin (100 mg/ml) were screened for correct insertion of the coding fragment by restriction analysis of the plasmid DNA. One of the isolated plasmids was sequenced on both strands with T7 and Sp6 primers by the dye primer method using an automated DNA sequencer (BioRad) following the manufacturer protocols and was used for later work.

To produce MF3 protein, the plasmid DNA of pMF was transformed into E. coli strains BL21 (DE3)—this strain synthesized T7 RNA polymerase; its expression level is regulated by the adding of IPTG.

EXAMPLE 21

Purification of MF3 Protein 100 ml of TB (terrific broth) in 1 l Erlenmeyer flask containing 100 mg/ml of ampicillin were inoculated with about 100 colonies of pMF3/BL21 (DE3) and incubated at 37° C. with shaking at 260 rpm in an orbital shaker "Certomat H" ("B. Braun Melsungen", Germany). At $A_{550nm}$ of 2-2.5, IPTG was added to get a final concentration of 0.05 mM while incubation was continued overnight at the same conditions. Next day cells were harvested by centrifugation at 4000 g for 30 min.

The pellet was resuspended in 50 ml of the following buffer: 50 mM Tris-HCl pH 8.0, 0.15 M NaCl, 2 mM EDTA, 2 µg/ml lysozyme, and incubated on ice for 30 min. Cleared lysate was loaded onto a column (25×50 mm) with Chelating Sepharose FF charged with Ni2+ (Pharmacia, Sweden) equilibrated with buffer A: 50 mM Tris-HCl pH 7.5 with 0.25 M NaCl. Sorbent was washed with 50 mM Tris-HCl, pH 7.5, 1 M NaCl. Bound proteins were eluted by linear gradient of increasing concentration of buffers:buffer A, 50 mM Tris-HCl, pH 7.5, 0.25 M NaCl; buffer B, 50 mM Tris-HCl pH 7.5, 0.25 M NaCl, 0.25 M imidazole. Flow rate was 3 ml/min and gradient volume 300 ml. MF3 was eluted at about 35% of buffer B.

Presence of MF3 in collected fractions was analyzed by SDS-PAGE. Fractions containing MF3 were combined and dialyzed against 20 mM Tris-HCl, pH 8.0. The protein solution was applied onto Mono Q HR10/10 column (Pharmacia, Sweden). Proteins were eluted by linear gradient of the increasing concentration of NaCl: buffer A, 50 mM Tris-HCl, pH 8.0; buffer B, 50 mM Tris-HCl, pH 8.0, 1M NaCl. Flow rate was 1 ml/min and gradient volume 60 ml. MF3 was eluted at about 40% of buffer B. Ammonium sulfate was added to the eluted protein for 25% saturation. Solution was centrifuged at 4000 g for 30 min and supernatant was loaded onto a Phenyl Sepharose HiLoad 16/10 column (Pharmacia, Sweden) equilibrated with 50 mM $Na_2HPO_4$. Proteins were eluted by linear gradient of the decreasing concentration of ammonium sulfate: from 0.5 M to 0.2 M for 30 min, from 0.2 M to 0 M for 60 min. Gradient volume was 200 ml and flow rate 2 ml/min. Buffer A was 50 mM $Na_2HPO_4$, pH 6.5, 1.7 M $(NH_4)_2SO_4$ and buffer B was MilliQ water. MF3 was eluted at about 95% of buffer B. Presence of MF3 in collected fractions was analyzed by SDS-PAGE. Fractions containing MF3 were combined, dialyzed against 50 mM ammonium acetate and lyophilized.

MF3 protein was dissolved in 1 ml of 50 mM Tris-HCl, pH8.0, and loaded on a column of 10×800 mm with Sephadex-G50 equilibrated with 50 mM ammonium acetate, pH 8.0. Fractions containing MF3 were combined and lyophilized. The yield of MF3 was about 200 mg from 1 l of the culture broth.

TB medium was prepared as follows: dissolve 12 g of Bacto Trypton, 24 g of Yeast Extract and 4 ml of Glycerol in 900 ml of water and autoclave. Cool to 60° C. and add 100 ml of sterile solution of 0.17 M $KH_2PO_4$, 0.72 M $K_2HPO_4$.

EXAMPLE 22

Gene Construction for Obtaining Transgenic Plants

T-DNA transfer to plant cells by *Agrobacterium*-mediated transformation was used for obtaining of transgenic plants. A plant binary vector, p13K, was constructed from pBin19 (Bevan, M. 1984) by cloning EcoRI fragments from pGL22/MF3 into EcoRI site of pBin19/The pGL22/MF3 contained the promoter and terminator of the cauliflower mosaic virus 35S transcript between which modified MF3 was cloned into BamHI site in place of the HPT gene (Pietrzak et al., 1986). Modification of the MF3 sequence was done by PCR on the B/H4 plasmid DNA with the followed primers:

5'-GGCCACCATGCTGATCGCCGCCAATAAGG (SEQ ID NO:7)

5'-√GGTCAGTGGTGATGGCCACCTTCG (SEQ ID NO:8)

Plasmid p13K was mobilised from *E. coli* to *Agrobacterium tumefaciens* LBA4404 by three-parental conjugation according Van Haute E. et. al, 1983.

EXAMPLE 23

*Agrobacterium*-Mediated Transformation of Potato

Plants (*Solanum tuberosum* cv. Nevskiy and cv. Lugovskoy) were obtained from the Centre "Bioengineering" Russian Academy of Sciences, as virus-free in vitro plantlets. The plants were propagated aseptically as single-node cuttings in 3×11.5-cm glass culture tubes on a standard propagation medium (PM) containing Murashige and Skoog's (1962) basal salt mixture (MS) supplemented with 20 g/l sucrose, 0.4 mg/l thiamine, 100 mg/l myo-inositol, 1.7 g/l phytagel (Sigma, St Louis, Mo. USA), pH 5.7. Plants were sub-cultured by transferring nodal segments to fresh medium every month, and a 5-mm long piece of stems (without leaves) were used as a source for the regeneration and transformation. These shoots were grown in a growth chamber with artificial light generated from a 50:50 mixture of Grow-Lux™ and fluorescent lights of 120 μE with a 16/8 h day/night cycle at 19° C.

The leaves were removed as close to the stem as possible and stems were placed in bunches of 20 and cut into 5 mm pieces and then explants were pre-cultured in 25-ml Petri dishes for 2 days in MS liquid medium without plant growth regulators. To inoculate the explants, pre-culture medium was removed by vacuum aspiration and diluted *Agrobacterium* solution was poured onto the stem pieces and held without agitation for 15 minutes. After this, the *Agrobacterium* solution was removed from the explants by vacuum aspiration and the explants were spread onto the co-culture plates using a spatula. About 100 explants were used per co-culture plate. Typically, this transformation system yielded 40 transgenic events per 100 explants. To minimize somaclonal variation the process was terminated before all transgenic events were harvested. Hence, a realistic yield of transgenic events was about 10 independent transgenic plants per 100 explants. Co-cultivation was in a culture room at 19° C. with a 16 h light cycle for 2 days.

Inoculations were made with the avirulent *A. tumefaciens* strain LBA4404 containing pBin13K, a derivative of pBin19. This plasmid has the nptII gene fused to the nopaline synthase promoter and terminator together with the mf3 gene fused to CaMV 35S RNA promoter and nopaline synthase terminator. Bacteria were grown at 28° C. in minimal A medium containing 50 mg/l kanamycin with constant shaking at 200 rpm overnight. On the day planned to inoculate the potato tissue, overnight bacteria culture was diluted 1:10 in MSO medium.

Stem explants were then transferred to Petri dishes with the regeneration medium, RM [MS-salts with 3% (w/v) sucrose and 2.0 mg/l glycine, 0.1 mg/l thiamine-HCL, 5.0 mg/l nicotinic acid, 0.5 mg/l pyridoxine-HCL, 0.05 mg/l D-biotin, 0.5 mg/l folic acid, 100 mg/l myo-inositol, 0.3 mg/l GA3, 5 mg/l ZR and 0.1 mg/l IAA], and incubated in the dark for 3 days. For the selection of transformants we used RM plus 100-150 mg/l kanamycin and 500 mg/l carbenicillin. The Petri dishes were stacked in a plastic bag, the top of the bag was closed, several holes were poked into the bag for ventilation and the bag was set in a culture room at 19° C. with a 16 h light cycle. Controls were treated in the same way but without *Agrobacterium* infection. The explants were transferred to fresh RM with antibiotics every 2 weeks. After four weeks, the explants had begun to form shoots from the callusing ends. The larger, normal-appearing shoots were cut from the callus. Only shoots that arose directly from callus were removed. Only one shoot per end of an explant was removed and then the explant was discarded.

Five shoots were placed in a Petri dish containing 50 ml of PM medium (supplemented with antibiotics) with their cut ends in the medium. After two weeks, healthy, growing, and rooting shoots were transferred to a new plate of PM medium, one plant per plate. After the second two weeks period, if the plants have not rooted, they were discarded.

Single node cuttings were maintained on PM medium in 25×150 mm culture tubes at 19° C. with a 16-h day cycle, one node per tube. In vitro grown plantlets were generally subcultured on a 3 to 4 week schedule. Plants destined to the greenhouse (last subculture) were grown for 7-10 days.

EXAMPLE 24

Tobacco Leaf Disc Transformation with *A. tumefaciens*

The plants (*Nicotiana tabacum* cv. Samsun NN) were propagated aseptically as single-node cuttings in 0.8 l glass flasks on A1. For sterile shoot culture, the top shoot with the apical meristem of the plant was removed, or the stem was cut into nodal sections containing an axillary bud, and then put onto A1 medium. The explants formed roots within 10-14 days. From the apical meristem or the axillary bud, a new shoot was growing into a plant.

The sterile shoot cultures were grown at 24° C., in a 16-h light/8-h dark rhythm with moderate light intensity. In vitro grown plantlets are generally subcultured on a 3 to 4 week schedule. Leaves were cut basally and transferred into Petri dish containing wet Whatman filter paper. Midrib of leaf was removed and leaf disks about 0.5 cm diameter were cut by sterile puncher. About 40-50 disks were placed upside-down in 9-cm Petri dish containing 10 ml of infection medium A2. A 2.5 ml of the *Agrobacterium* AGL0 culture containing pBin13K was added to each Petri dish (pBin13K is a derivative of pBin19). This plasmid has the nptII gene fused to the nopaline synthase promoter and terminator together with the MF3 gene fused to CaMV 35S RNA promoter and nopaline synthase terminator. Bacteria were grown at 28° C. in minimal A medium containing 50 mg/l kanamycin with constant shaking at 200 rpm until turbidity of approximately 0.6 (600 nm) was reached. After 15-20 min leaf explants were blotted onto sterile Whatman filter paper, transferred to Petri dishes with the abaxial surface in contact with infection medium A2 supplemented with 8 g/l washed agar and incubated in the growing chamber with low light intensity. After 3 days leaf disks were washed in Petri dishes with infection medium A2 containing 500 mg/l carbenicillin, then blotted onto sterile Whatman filter paper and transferred to Petri dishes with callus-induction medium A3 containing 100 mg/l kanamycin, 500 mg/l carbenicillin. The explants were incubated at 24° C., at low light intensity, with 16-h day/8-h night rhythm. Leaf disks were subcultured on fresh A3 medium weekly. After 3-4 weeks, regenerating calli were separated from the leaf disks and put onto A4 medium with 100 mg/l kanamycin. Two to three weeks later, shoots were cut off from the calli and transferred to the rooting medium A5 containing 100 mg/l kanamycin. Rooted shoots were propagated as sterile shoot cultures on A1 medium or transferred to soil in the greenhouse.

It will be clear to those having skill in the art that many changes may be made in the above-described details of preferred embodiments of the present invention without departing from the underlying principles thereof. The scope of the present invention should therefore be determined only by the following claims.

The invention claimed is:

1. A bioactive polypeptide, MF3, with a primary structure depicted in SEQ ID NO: 1, or an active fragment of MF3 according to SEQ ID NO: 3 or SEQ ID NO:4, said polypeptide, or active fragment being capable of effecting a resistance of a plant against microbial diseases and/or against attack of plant parasites.

2. An isolated DNA sequence according to SEQ ID NO: 2 encoding a bioactive polypeptide MF3 having amino acid sequence according to SEQ ID NO: 1.

3. A method of acquiring resistance of a plant against microbes and/or plant parasites by introducing bioactive polypeptide MF3 having an amino acid sequence SEQ ID NO:1, or an active fragment having an amino acid sequence SEQ ID NO:3 or SEQ ID NO:4, into plants mechanically or by means of carrier molecules.

4. The method according to claim 3, wherein the carrier is chitosan.

5. A vector comprising the DNA according to claim 2.

6. A transgenic plant or plant cell culture comprising the vector according to claim 5.

7. A host cell stably transformed with the vector of claim 5.

8. A plant protectant composition comprising isolated bioactive polypeptide MF3 having an amino acid sequence according to SEQ ID NO: 1, an isolated active fragment of MF3 having an amino acid sequence according to SEQ ID NO:3 or SEQ ID NO:4.

9. A method of isolating and purifying the bioactive polypeptide of claim 1 from bacterial cells expressing said bioactive polypeptide, the method comprising the steps:

a) cultivating and extracting the bacterial cells with a buffer solution by heating to an elevated temperature;

b) precipitating a crude MF3 polypeptide at low temperature with a precipitant;

c) fractionating re-dissolved precipitate comprising the polypeptide of step b through an anion exchange chromatography column and collecting fractions with anti-microbial, anti-nematode, or anti-insect activities;

d) performing polyacrylamide gel electrophoresis to the polypeptide fractions with anti-microbial, anti-nematode, or anti-insect activities; and e) recovering an isolated polypeptide eluted from the gel of step d.

10. A method to protect plants or plant cell cultures from microbial diseases or pests by applying the protectant composition of claim 8.

11. The method according to claim 10, wherein the plants or plant cell cultures are protected from diseases caused by a microbe selected from the group consisting of *Phytophtora infestans, Erwinia carotovora, Pyricularia oryzae, Fusarium cumorum, Septoria nodorum*, Tobacco Mosaic Virus, Potato Virus X, and Potato Virus Y.

12. The method according to claim 10, wherein the plants are protected from potato cyst nematodes.

13. The transgenic plant or plant cell culture of claim 6, wherein the transgenic plant or cell culture expresses increased resistance against a disease caused by a microbe selected from the group consisting of *Phytophtora infestans, Erwinia carotovora, Pyricularia oryzae, Fusarium cumorum, Septoria nodorum*, Tobacco Mosaic Virus, Potato Virus X, and Potato Virus Y.

14. The transgenic plant or plant cell culture of claim 6, wherein the transgenic plant or cell culture expresses increased resistance against potato cyst nematodes.

15. An isolated DNA sequence encoding an active fragment of bioactive polypeptide MF3, said active fragment having an amino acid sequence according to SEQ ID NO:3 or SEQ ID NO:4.

* * * * *